United States Patent [19]
Tsuji et al.

[11] Patent Number: 6,015,680
[45] Date of Patent: Jan. 18, 2000

[54] HUMAN LUNG ADENOCARCINOMA-RELATED MONOCLONAL ANTIBODY AND IMMUNOASSAY METHOD WHICH USES THE SAME

[75] Inventors: Kouichi Tsuji; Yoshihiro Yoshida; Takashi Uwano, all of Kanagawa, Japan

[73] Assignee: Terumo Kabushiki Kaisha, Tokyo, Japan

[21] Appl. No.: 08/913,315

[22] PCT Filed: Mar. 13, 1996

[86] PCT No.: PCT/JP96/00613

§ 371 Date: Sep. 12, 1997

§ 102(e) Date: Sep. 12, 1997

[87] PCT Pub. No.: WO96/28569

PCT Pub. Date: Sep. 19, 1996

[30] Foreign Application Priority Data

Mar. 13, 1995 [JP] Japan ................................ 7-052260
Apr. 20, 1995 [JP] Japan ................................ 7-094071

[51] Int. Cl.[7] .................. A61K 39/395; G01N 33/53; C07K 16/30
[52] U.S. Cl. .................. 435/7.23; 435/329; 435/344; 435/183; 530/387.7; 530/387.5; 530/388.8; 530/389.7; 530/387.3; 530/391.3; 530/387.1; 424/133.1; 424/137.1; 424/138.1; 424/174.1; 424/155.1; 424/178.1
[58] Field of Search ................ 530/387.7, 388.8, 530/389.7, 387.3, 387.5, 391.3; 424/138.1, 155.1, 174.1, 137.1, 178.1; 435/7.23, 329, 344

[56] References Cited

U.S. PATENT DOCUMENTS 4,474,893 10/1984 Reading et al. .
4,722,899 2/1988 Hamaoka et al. .
5,552,291 9/1996 Yoshida et al. .

FOREIGN PATENT DOCUMENTS 63-19561 1/1988 Japan .
63-222700 9/1988 Japan .
2-72198 3/1990 Japan .

OTHER PUBLICATIONS

Sevier et al Clin Chem vol. 27/11 1797, 1981.
Delente Trends in Biotechnology vol. 3 No. 9 12, 1985.
Hakomori et al Cancer Research vol. 45 2405–2414, Jun. 1985.
Walker Lectins vol. 6591, Jul. 1987.
Maimonis et al Cancer Research vol. 50 6718, Oct. 1990.
Seaver Genetic Engineering News vol. 10 10 and 21, Aug. 1994.
Knight Biotechnology vol. 7/1 35, Jan. 1989.
Bird et al Science vol. 242 423, Oct. 1988.
Johnstone et al Immunochemistry in practice Blackwell scientific Publications 52–60, 1982.
Paul WE Chapter 8 Fundamental Imunology Raven Press NY 242, 1993.
Maimonis, Peter, et al., "Detection and Characterization of a High Molecular Weight Human Lung Carcinoma–associated Glycoprotein." *Cancer Research* 50, Oct. 15, 1990, pp. 6738–6743.

*Primary Examiner*—Julie Reeves
*Attorney, Agent, or Firm*—Burns, Doane, Swecker & Mathis, LLP

[57] ABSTRACT

The monoclonal antibody produced by a hybridoma cell strain TRD-L1, -L2 or -L3 which is obtained by the fusion between mouse myeloma cells and spleen cells of a mouse immunized with a human lung adenocarcinoma cell secretion component reacts in a specific fashion with a glycoprotein antigen that has a molecular weight of 200 kD or more (SDS-PAGE) and is present in human lung adenocarcinoma cells. It can be used efficiently in cancer diagnosis.

9 Claims, 10 Drawing Sheets

(A) Pas staining (B) immunoblotting

HUMAN LUNG ADENOCARCINOMA-RELATED MONOCLONAL ANTIBODY AND IMMUNOASSAY METHOD WHICH USES THE SAME

This application is a 35 U.S.C. 371 national stage filing of international application PCT JP96/00613 filed Mar. 13, 1996.

TECHNICAL FIELD

Human lung carcinoma is classified into four principal histological types. That is, lung adenocarcinoma, squamous cell carcinoma, small cell carcinoma and large cell carcinoma. This invention relates to a monoclonal antibody having reactivity with human lung adenocarcinoma, to a glycoprotein antigen recognizable by this antibody and to a detection method and a therapeutic drug of human lung adenocarcinoma in which the monoclonal antibody is used. Also, this invention can be used in the diagnosis and treatment of human lung adenocarcinoma and is applicable to the field of diagnostic drugs and therapeutic drugs of lung adenocarcinoma.

BACKGROUND ART

As a detection method of lung adenocarcinoma, a method has been known in which human lung adenocarcinoma is detected by measuring it using antibodies for carcinoembryonic antigen (CEA) and sialyl SSEA-1 (SLX) known as tumor markers. However, in the diagnostic method which detects these tumor markers, not only the positive ratio on lung adenocarcinoma is 40 to 50% but also they are detected in other tissue type of lung carcinoma, benign lung diseases and other organ cancers including colon cancer, stomach cancer and breast cancer. On the other hand, Maimonis P. et al. (*Cancer Res.*, 50, 6738 (1990)) have reported a monoclonal antibody DF-L1 obtained using a lung adenocarcinoma tissue as the immunogen. However, the antigen which is detected using this antibody is present in sera of patients of not only lung adenocarcinoma but also squamous cell carcinoma, breast cancer and the like.

Thus, the monoclonal antibodies so far developed can hardly be regarded as diagnostic means specific for lung adenocarcinoma and are nor sufficient for screening, definite diagnosis and monitoring of metastasis, recidivation. In addition, lung cancers have different properties in terms of cell proliferation, development and the like, due to different tissue type of each lung cancer. Because of this, the corresponding therapeutic method varies depending on each tissue type. In consequence, it is extremely important to find an antigen and an antibody peculiar to lung adenocarcinoma for the diagnosis of lung adenocarcinoma, and furthermore, for the treatment of lung adenocarcinoma.

DISCLOSURE OF THE INVENTION

Taking the aforementioned actual circumstances into consideration, the inventors of the present invention have conducted intensive studies on lung adenocarcinoma cells and found as the result a high molecular weight glycoprotein which is peculiarly present in the culture broth of an established lung adenocarcinoma cell line Calu-3 (ATCC HTB-55) and in sera of lung adenocarcinoma patients but is hardly detectable in normal human sera, from glycoproteins which are present in the culture broth of the established lung adenocarcinoma cell line Calu-3 (ATCC HTB-55) and can perform cross reaction with the monoclonal antibody DF-L1 prepared by Maimonis P. et al. (*Cancer Res.*, 50, 6738 (1990)). Also, hybridomas TRD-L1, TRD-L2 and TRD-L3 were established using this glycoprotein as the immunogen, and antibodies produced by these cells were obtained. Thereafter, the present invention has been accomplished by further finding that, when said monoclonal antibodies are used, a lung adenocarcinoma-originated antigen can be isolated and said antigen can be measured accurately.

The present invention is as follows.

(1) A monoclonal antibody whose antigen is a secretory glycoprotein specific for human pulmonary adenocarcinoma cell having a molecular weight of 200 kD or more (SDS-PAGE).

(2) The monoclonal antibody according to the above item (1) wherein said glycoprotein reacts with MAA lectin and PNA lectin but not with GNA lectin, SNA lectin and DSA lectin.

(3) The monoclonal antibody according to the above item (1) or (2) wherein its isotype is IgM.

(4) The monoclonal antibody according to any one of the above items (1) to (3) wherein it is produced by a hybridoma cell strain TRD-L1 (original designation FERM P-14878 assigned by National Institute of Bioscience and Human Technology, Agency of Industrial Science and Technology, Higashi 1-1-3, Tsukuba-shi, Ibaraki, Japan, which has been transferred to the authority on Feb. 8, 1996, under Budapest Treaty (designation FERM BP-5383)), TRD-L2 (designation FERM P-14879 assigned by National Institute of Bioscience and Human Technology, Agency of Industrial Science and Technology) or TRD-L3 (designation FERM P-14880 assigned by National Institute of Bioscience and Human Technology, Agency of Industrial Science and Technology) obtained by the fusion between mouse myeloma cells and spleen cells of a mouse immunized with a human lung adenocarcinoma cell secretion component.

(5) The monoclonal antibody according to any one of the above items (1) to (4) wherein the antibody is an Fab, F(ab')$_2$ or Fv fragment.

(6) The monoclonal antibody according to any one of the above items (1) to (5) wherein it is linked with a marker which can generate a detectable signal.

(7) The monoclonal antibody according to the above item (6) wherein said marker is an enzyme, a radioactive material, a fluorescent material or a metal colloid illuminant.

(8) A secretory glycoprotein specific for human pulmonary adenocarcinoma cell having a molecular weight of 200 kD or more (SDS-PAGE), and which is the glycoprotein to which the monoclonal antibody of the above item (4) specifically binds.

(9) The glycoprotein according to the above item (8) wherein it further reacts with MAA lectin and PNA lectin but does not react with GNA lectin, SNA lectin and DSA lectin.

(10) An immunoassay method for cancer diagnosis use which comprises using the monoclonal antibody of any one of the aforementioned items (1) to (7).

(11) The immunoassay method for cancer diagnosis use according to the above item (10) wherein the glycoprotein of the aforementioned item (8) or (9) is measured using the monoclonal antibody of any one of the aforementioned items (1) to (7).

(12) An immunoassay kit for use in internal cancer diagnosis to specify cancers and their metastatic regions, which uses the monoclonal antibody of any one of the aforementioned items (1) to (7).

(13) The glycoprotein antigen of the aforementioned item (8) or (9) which is a cancer vaccine.

(14) A monoclonal antibody in which a drug for cancer treatment use is linked to the monoclonal antibody of any one of the aforementioned items (1) to (7).

(15) A method for treating lung adenocarcinoma, which comprises administering a cancer vaccine.

OUTLINE OF THE INVENTION

Figure 1:
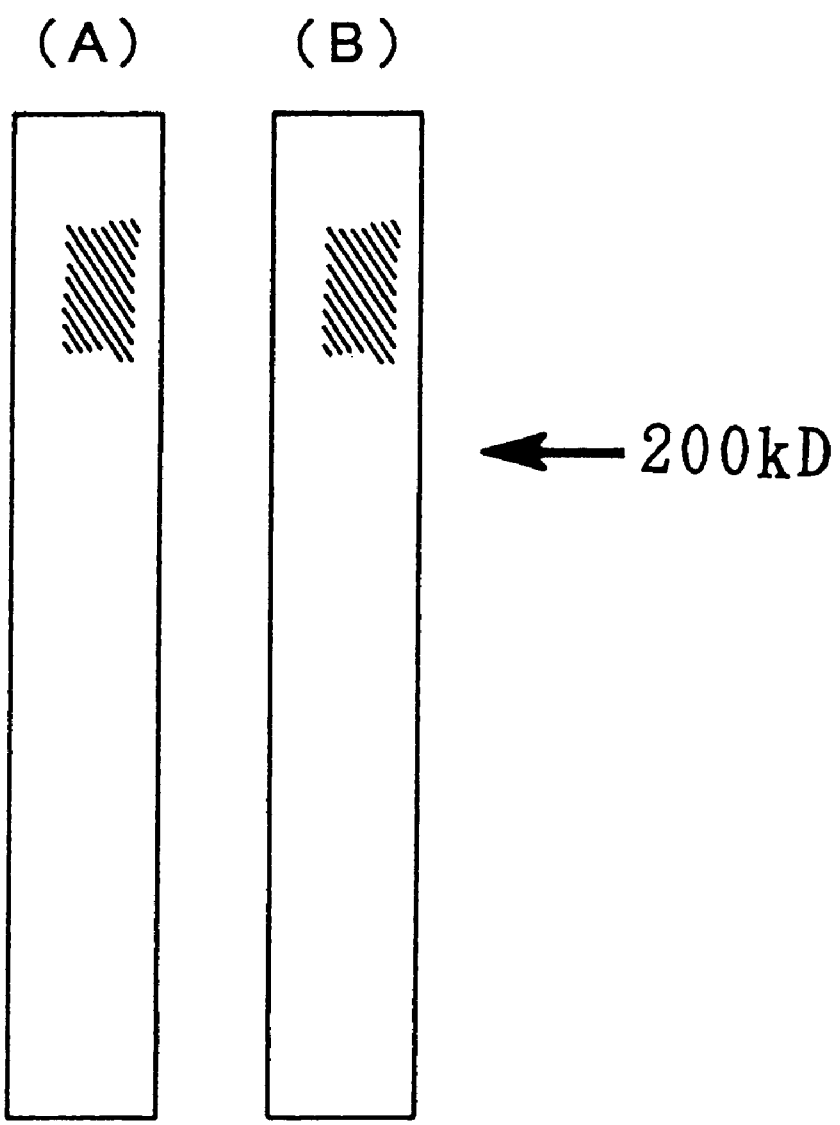
FIG. 1 shows photographs of electrophoresis as schematic illustration, in which FIG. 1 (A) shows a result of PAS staining and FIG. 1 (B) shows a result of immunoblotting.

The following describes the present invention in detail. First, mouse spleen cells prepared using a glycoprotein as the immunogen which is present in the culture broth of the established lung adenocarcinoma cell line Calu-3 (ATCC HTB-55) and can perform cross reaction with the monoclonal antibody DF-L1 are subjected to cell fusion with mouse myeloma cells, thereby preparing hybridomas, subsequently selecting a hybridoma capable of producing a monoclonal antibody having low reactivity with a protein recognizable by DF-L1 which is present in normal human serum and having high reactivity with a protein that exists in the culture broth of Calu-3 (ATCC HTB-55). This hybridoma is further cultured in a medium or administered into the abdominal cavity of mice to effect formation of ascitic fluid. The present invention provides a monoclonal antibody obtained from the culture broth or ascitic fluid and an antigen which can be recognized by this antibody. It also provides a method for the measurement of said antigen making use of said monoclonal antibody.

More illustratively, it provides a monoclonal antibody which is produced by a hybridoma TRD-L1, TRD-L2 or TRD-L3, belongs to the class IgM and reacts with lung adenocarcinoma cells, said monoclonal antibody being able to recognize a glycoprotein having a molecular weight of 200 kD or more. The following describes a production method of the monoclonal antibody of the present invention in detail.

(1) Preparation of immunogen

An established lung adenocarcinoma cell line, such as Calu-3 (ATCC HTB-55) for example, is cultured in RPMI 1640 medium or MEM medium and then the culture supernatant fluid is recovered. After removing insoluble matter from the thus recovered culture supernatant fluid by centrifugation or using a filter, this is applied to a monoclonal antibody DF-L1-linked affinity chromatography column to effect adsorption of the antigen in the culture supernatant fluid. After subsequent washing with PBS, the elution is effected using 3 M KSCN. After the elution, dialysis and concentration are carried out and then the lung adenocarcinoma established cell-originated antigen comprised of a glycoprotein fraction of 200 kD or more in molecular weight is recovered using a gel chromatography column and used as the immunogen.

(2) Immunization of animals and preparation of hybridoma cells

Mice of 3 to 10 weeks of age, preferably 6 weeks of age, are immunized using the just described antigen derived from the lung adenocarcinoma established cell line as the immunogen to prepare hybridoma cells from spleen lymph node and peripheral blood. With regard to the immunization method, the immunogen (1 to 100 µg/animal) is administered, together with an appropriate adjuvant such as Freundis complete adjuvant, Freundis incomplete adjuvant or pertussis vaccine, subcutaneous or into the abdominal cavity of the animals. Thereafter, the immunogen is administered 2 to 5 times at intervals of 1 to 2 weeks. In subjecting to cell fusion, the immunogen is administered to the immunized mice (1 to 100 µg/animal) 3 to 4 days prior to the fusion treatment and then spleen tissues are excised to prepare spleen cells.

(3) Myeloma cells

An established cell line is used as the myeloma cells. For example, though not particularly limited, 8-azaguanine-resistant mouse (BALB/c) myeloma cell strains P3-X63Ag8-U1, SP2/O-Ag4, PC-X63-Ag8 and the like are desirable.

(4) Cell fusion

Cell fusion is effected by mixing myeloma cells and antibody producer cells generally in RPMI medium, MEM medium or the like medium. They are mixed in such a ratio that the number of cells becomes antibody producer cells- :myeloma cells=5–10:1 and centrifuged and then the thus precipitated cells are thoroughly loosened and subjected to fusion using polyethylene glycol while stirring or using an electrofusion apparatus. The polyethylene glycol to be used may preferably have a molecular weight of 1,000 to 6,000. Selection of fused cells is carried out using HAT medium.

(5) Selection of hybridoma

Selection of hybridoma is carried out and checking culture medium of hybridomas by the following enzyme immunoassay or the like means. Since this method is merely an example of the checking method, the present invention is not restricted by this method, and various alterations and modifications can be made.

Enzyme immunoassay

The aforementioned Calu-3 cancer cell-derived antigen (protein, 0.5 to 5 µg/ml) is dispensed in 50 to 200 µl portions into wells of a 96 F aminoplate, a normal human serum-derived antigen (protein, 0.5 to 5 µg/ml) is distributed in 50 to 200 µl/well portions in the same manner, and their respective bonding is effected using glutaraldehyde in the usual way. After removing the supernatant fluid by suction, each of the plates is washed with PBS-Tween 20 and block (blocking) of the bound residues is carried out by adding 300 µl of 1% BSA-PBS. After removing the supernatant fluid by suction, the plate is washed with PBS-Tween 20. A hybridoma culture supernatant fluid is dispensed in 40 to 100 µl portions into wells of the plate and allowed to undergo the reaction overnight at 4° C. or for 1 hour at 37° C. After removing the supernatant fluid by aspiration, the plate is washed with PBS-Tween 20. After the washing, an anti-mouse immunoglobulin antibody-peroxidase conjugate is dispensed in 100 μl portions into the wells to carry out 1 hour of reaction at 37° C. After the reaction, the plate is again washed, dispensed with 0.1 M citrate buffer (pH 4.2) containing O-phenylenediamine dihydrochloride or tetramethylbenzidine and hydrogen peroxide in 100 μl/well portions and then allowed to stand for 30 minutes at room temperature. After stopping the reaction by dispensing 2 N sulfuric acid in 50 μl/well portions, OD at 492 nm or OD at 450 nm is measured. In this case, a hybridoma having higher reactivity with the cancer cell strain-derived antigen than that with the normal human serum-derived antigen is selected.

A hybridoma which produces the monoclonal antibody of the present invention is obtained by carrying out cloning of the thus obtained antibody producing hybridoma by limiting dilution analysis or the like means. In order to produce the monoclonal antibody of the present invention in a large amount making use of the thus obtained hybridoma, as a first step, the cells are cultured in a large scale or, alternatively, pristane or the like mineral oil is administered into the abdominal cavity of mice, subsequently carrying out intraperitoneal administration of said hybridoma, and then the ascitic fluid is collected several days thereafter. Next, the monoclonal antibody is separated and purified from the thus obtained culture broth or ascitic fluid for example in accordance with the usual antibody separation purification techniques. The thus obtained monoclonal antibody of the present invention reacts with the human lung adenocarcinoma-derived glycoprotein but hardly with the normal human-derived glycoprotein.

The monoclonal antibody of the present invention produced by the hybridoma TRD-L1, TRD-L2 or TRD-L3 obtained in this manner can be classified as IgM isotype, but the antibody is not necessarily in its intact form after its production by the cells and may be in the form of Fab, F(ab)2, Fv or the like useful fragment. Such a useful fragment can be obtained from its original antibody by its peptidase hydrolysis using papain or pepsin. The term useful fragment means that it can bind to the binding site of the antigen of the same origin in competition with the original antibody. However, the above examples of the monoclonal antibody of the present invention are unique isotype antibodies which bind to specific determining sites on respective antigens and are derived from mice, though not particularly limited thereto. In consequence, the monoclonal antibody of the present invention which is derived from mouse, human or the like mammals or other origin or any combination thereof can be used, provided that the antibody has a function to bind to the specified specific determining site on the specified antigen in the same manner. Also, even when isotype of the antibody is IgG, IgA, IgE or the like other class, it can be used in the same manner.

(6) Preparation of antigen

The human lung adenocarcinoma-derived antigen to be obtained by the present invention can be produced for example by making use of the monoclonal antibody of the present invention which is obtained in the aforementioned manner. That is, it can be produced from sera of lung adenocarcinoma patients or cells of a lung adenocarcinoma established cell line. For example, Calu-3 (ATCC HTB-55) is cultured in RPMI 1640 medium or MEM medium and the culture supernatant fluid is recovered, or serum of a lung adenocarcinoma patient is obtained in the usual way. Insoluble matter is removed from the thus recovered culture supernatant fluid or serum of a lung adenocarcinoma patient by centrifugation or using a filter, and the resulting sample is applied and adsorbed to an affinity chromatography column whose packing is linked by the monoclonal antibody of the present invention. After washing with an appropriate buffer (PBS for example), elution is carried out with 3 M KSCN. After the elution, dialysis and concentration are carried out and then fractions of 200 kD or more in molecular weight are recovered using a gel filtration chromatography column. The antigen obtained in this manner has a molecular weight of about 200 kD or more (SDS-PAGE) and is a sugar chain-containing glycoprotein, because it is stained by PAS staining. The human lung adenocarcinoma-derived antigen obtained in this manner can be used in the treatment of human lung adenocarcinoma as an attenuated vaccine or an inactivated vaccine.

(7) Detection of antigen

In order to measure the antigen of the present invention using an antibody specific for the antigen of the present invention, it can be carried out in accordance with a known immunoassay method, for example to measure the presence of a malignant state in the lung tissue. The term malignant state means the presence of atypical tumor cells and the like simultaneously including a cancer. The presence of a tumor in a sample is confirmed by allowing the sample to react with the monoclonal antibody of the present invention and then detecting an immune complex linked to the sample. An example of the present invention is a method for the detection of tumor cells in excised tissues. A tumor section obtained by excision is fixed on a slide glass in the usual way. The thus obtained tumor section is allowed to react with the monoclonal antibody of the present invention. With regard to the reaction conditions, the reaction is carried out for example in an appropriate container such as a Petri dish. After removing non-specifically bound antibodies by washing, subsequent reaction is carried out with a second antibody which can react with said antibody and is labeled with a detectable marker. The marker is a substance which can generate a detectable signal, such as a radioactive element, a fluorescent material, an enzyme or the like. Since binding of the antibody reflects the presence of a malignant material, the presence of the malignant material can be confirmed by detecting the detectable signal. In addition, binding of said monoclonal antibody to a sample can also be measured by using the monoclonal antibody to which a radioactive material, an enzyme or the like marker capable of generating a detectable signal is linked by covalent bonding. Covalent bonding of a marker to the antibody or antibody fragment can be effected by a usually used method. In this connection, this method is not limited to excised tissues, and it can be used in the detection of cancer cells in sputum, alveoli wash solution and the like.

When an antibody specific for the antigen of the present invention is used, the antigen of the present invention in human secretions (blood, urine, sputum and the like) can be measured. This measurement can be carried out in accordance with a known immunoassay method. Examples of the antibody specific for the antigen of the present invention include both polyclonal and monoclonal antibodies which can be used alone or a combination thereof. Examples of the immunoassay include enzyme immunoassay, radioimmunoassay, fluoroimmunoassay, chemiluminescence/bioluminescence immunoassay, latex agglutination immunoassay and the like. As the enzyme immunoassay, optional known modifications can be used. For example, the antigen can be measured directly or competitively making use of a homogenous phase enzyme immunoassay, a solid phase method, a heterogeneous enzyme immunoassay, a sandwich enzyme immunoassay and the like. Of these methods, sandwich enzyme immunoassay is particularly desirable. In this method, a monoclonal antibody linked to a solid carrier is allowed to react with a test solution and then, after washing, a solution of an enzyme-labeled monoclonal or polyclonal antibody which has reactivity with the antigen is dispensed. After washing, amount of the antigen in the sample is measured based on the enzyme-substrate reaction. In this connection, the monoclonal antibody to be used in the latter reaction is desirably an antibody which can bind to a site which is different from the specific binding site recognizable by the monoclonal antibody linked to the solid carrier, except for a case in which the antigen has a plurality of sites to which the solid phase monoclonal antibody can be linked. Examples of the carrier to be used include a microplate, a test tube, beads or fine particles made of polystyrene, polyethylene or polyvinyl chloride, a test tube, beads or a filter paper made of glass, or a sheet of dextran, cellulose acetate or cellulose, as well as similar materials thereof. Also, examples of the desirable enzyme to be used in the enzyme immunoassay of the present invention include horseradish peroxidase, alkaline phosphatase, β-galactosidase and the like. Examples of other assay methods of the present invention include radioimmunoassay in which a radioactive marker is used, fluoroimmunoassay in which a fluorescent marker is used, chemiluminescence/bioluminescence immunoassay in which a luminescent marker is used and latex agglutination immunoassay in which a latex marker is used.

In carrying out the present invention, it is desirable to prepare in advance an assay kit which comprises a combination of the monoclonal antibody of the present invention, the antigen of the present invention and other accessories. For example, in the case of sandwich enzyme immunoassay, it contains a monoclonal antibody linked to an appropriate carrier, a freeze-dried preparation or a solution of an enzyme-labeled monoclonal antibody which can bind to the same antigen together with the monoclonal antibody or of a polyclonal antibody labeled with the enzyme in the same manner, a standard solution of purified antigen, a buffer solution, a washing solution, pipettes, a reaction container and the like. In this connection, the polyclonal antibody to be used in the assay of the present invention can be collected easily from an animal immunized against the antigen of the present invention in the usual way. For example, a rabbit is immunized several times using the antigen of the present invention, and when the antibody titer against said antigen reaches maximum, blood is collected to separate and purify the antibody fraction in the usual way.

(8) Internal diagnosis

The antibody of the present invention can be applied to a method in which primary and metastatic layers of lung adenocarcinoma in a patient are transformed into images, in accordance with a known technique on malignant melanoma (Larson S. M. et al., *J. Clin. Invest.*, 72, 2101 (1983)). The antibody or a fragment thereof is labeled with a radioactive material and administered to a patient by intravenous injection, and then the affected parts of the patient are transformed into images making use of PET method or the like. Examples of the material for radioactive labeling include 99-Tc, 131-I and 125-I.

In addition, the monoclonal antibody of the present invention may be used as a diagnosis kit for the practice of the aforementioned methods. An example of such a case is a combination of the monoclonal antibody and a marker-linked material which can detect the antigen, or the monoclonal antibody labeled with a detectable marker. Said diagnosis kit contains a buffer solution necessary for the detection method and a protein stabilizing agent such as a polysaccharide, and an active substance for reducing background interference in the assay, a control reagent, a test apparatus and the like may also be used as occasion demands.

(9) Therapeutic method

The monoclonal antibody of the present invention can also be used in the treatment of lung adenocarcinoma, for example by pharmaceutically combining it with a variety of toxins having toxicity to cancer cells, an anticancer drug or a radioactive material in accordance with a known method. In addition, a method in which a patient is immunized against the antigen of the present invention in its purified form, a fragment of said antigen or a modified form of said antigen can be exemplified as a method for providing immunological antitumor activity.

EXAMPLES

The following describes the present invention further in detail with reference to examples.

Inventive Example 1

Preparation of monoclonal antibody

An established lung adenocarcinoma cell line, Calu-3 (ATCC HTB-55), was cultured in RPMI 1640 medium containing 5% FBS and then the culture supernatant fluid was recovered. The thus recovered culture supernatant fluid was centrifuged and the insoluble matter was removed using a 0.45 μm filter, and then the thus prepared sample was applied to an affinity chromatography column whose packing has been linked by a monoclonal antibody DF-L1, thereby effecting adsorption of the antigen. After subsequent washing with 10 mM PBS (phosphate buffer, pH 7.4), the elution was effected using 3 M KSCN. After the elution, the eluate was dialyzed and concentrated and then fractionated by a gel chromatography using Sephacryl S-300 (manufactured by Pharmacia) to recover and concentrate a fraction of 200 kD or more in molecular weight. The thus obtained glycoprotein was used as the immunogen. This was made into an emulsion with Freundis complete adjuvant and Freundis incomplete adjuvant, and 1 μg of it was subcutaneously administered to a BALB/c mouse of 6 weeks of age. The immunization step was repeated three times at intervals of 2 weeks, and the final immunization was effected by intravenous injection of the same amount of the aforementioned glycoprotein. Three days thereafter, the spleen was aseptically excised to prepare $2.5 \times 10^7$ of spleen cells. After hemolysis of contaminated erythrocytes with Geyis solution, the cells were washed twice with RPMI 1640 medium.

Antibody non-producing SP2/0-Ag4 mouse myeloma cells were used in the subsequent cell fusion. The SP2/0-Ag4 cells were cultured and maintained in RPMI 1640 medium containing 10% fetal calf serum (FCS, manufactured by Flow) contained in a culture flask (manufactured by Sumitomo Bakelite), and the cells at logarithmic growth phase were used in the cell fusion. The myeloma cells were recovered, adjusted to a density of $5 \times 10^6$ cells and then washed twice with RPMI 1640 medium. The washed spleen cells and myeloma cells were thoroughly mixed in a fusion buffer and subjected to 5 minutes of centrifugation at 1,000 rpm to remove the culture solution. The resulting pellet was again suspended in the fusion buffer. The cell fusion was carried out by an electrofusion method using a cell fusion apparatus (SSH-2, manufactured by Shimadzu Corp.). After the cell fusion, the cells were recovered in a container which contained 30 ml of RPMI medium supplemented with 10% FCS and then cultured for 30 minutes under conditions of 37° C. and 5% $CO_2$/95% air. After 5 minutes of centrifugation at 1,000 rpm, the cells were re-suspended in RPMI 1640 medium containing 10% FCS and 10% HCF (manufactured by ORIGEN) and dispensed in 0.1 ml portions into wells of a 96 F plate (manufactured by Costar). This was cultured under conditions of 37° C. and 5% $CO_2$/95% air, and a HAT selection was carried out on the next day by adding 0.1 ml of HAT medium (RPMI 1640 medium containing 10% FCS, hypoxanthine, aminopterin and thymidine). After the fusion, half the volume of the medium was exchanged with HAT medium on the fourth day, and the culture supernatant fluids were collected on the tenth day to measure their antibody activity using an enzyme immunoassay method.

The immunoassay was carried out in the following manner. That is, the cancer cell-derived antigen and the same amount of a normal human serum-derived antigen (antigen containing 1 μg/ml of protein) were dispensed in 100 μl portions into wells of a 96 F aminoplate, and their bonding was effected using glutaraldehyde in the usual way. After removing the supernatant fluid by suction, the plate was washed with PBS-Tween 20, and block (blocking) of the bound residues was carried out by adding 300 μl of 1% BSA-PBS. After removing the supernatant fluid by suction, the plate was washed with PBS-Tween 20. A hybridoma culture supernatant fluid was dispensed in 50 μl portions into wells of the plate and allowed to undergo 1 hour of reaction at 37° C. After removing the supernatant fluid by suction, this was again washed with PBS-Tween 20. After the washing, an anti-mouse immunoglobulin antibody-peroxidase conjugate was dispensed in 100 μl portions into the wells to carry out 1 hour of reaction at 37° C. After washing, 0.1 M citrate buffer (pH 4.2) containing O-phenylenediamine dihydrochloride or tetramethylbenzidine and hydrogen peroxide was dispensed in 100 μl/well portions and then allowed to stand for 30 minutes at room temperature. After stopping the reaction by dispensing 2 N sulfuric acid in 50 μl/well portions, OD at 492 nm was measured (OD 450 nm in the case of TMBZ). In this case, a hybridoma having higher reactivity with the cancer cell strain-derived antigen than that with the normal human serum-derived antigen was selected.

A hybridoma capable of producing the monoclonal antibody of the present invention was obtained by carrying out cloning of the thus obtained antibody producing hybridoma by limiting dilution analysis or the like means. In order to produce the monoclonal antibody of the present invention in a large amount making use of the thus obtained hybridoma, the cells were cultured in a large scale. Next, the monoclonal antibody of the present invention was separated and purified from the thus obtained culture broth in accordance with the usual antibody separation purification techniques. The thus obtained monoclonal antibody of the present invention reacts with human lung adenocarcinoma but hardly with normal human. When its isotype was confirmed using an isotype kit (manufactured by Bio-Rad), said antibody was classified as IgM isotype.

Inventive Example 2

Purification of antigen

The established lung adenocarcinoma cell line, Calu-3 (ATCC HTB-55), was cultured in RPMI 1640 medium containing 5% FBS and then the culture supernatant fluid was recovered. The thus recovered culture supernatant fluid was centrifuged, the insoluble matter was removed using a 0.45 μm filter, the thus prepared sample was applied to an affinity chromatography column whose packing has been linked by the monoclonal antibody TRD-L1, TRD-L2 or TRD-L3 in the usual way, thereby effecting adsorption of the antigen, and then the column was washed with 10 mM PBS (phosphate buffer, pH 7.4). After the washing, the elution was effected using 3 M KSCN. After the elution, the eluate was dialyzed and concentrated and then fractionated by a gel chromatography using Sephacryl S-300 (manufactured by Pharmacia) to recover and concentrate a fraction which reacted with the antibody.

Inventive Example 3

Biochemical properties of antigen

Each of the antigens reactive with TRD-L1, TRD-L2 and TRD-L3 was analyzed by SDS-polyacrylamide gel electrophoresis, Western immunoblotting analysis, lectin analysis and PAS staining. Purified antigen was separated on 4% gel by the Laemmli method in the usual way. A portion of the gel was used in PAS staining. The results thus obtained are shown in FIG. 1 (A). In the lectin analysis, an antigen purified in the same manner from normal human serum using DF-L1 was also analyzed in the same manner.

In this connection, Western immunoblotting was carried out in the following manner. That is, separated protein was transferred on a PVDF membrane (manufactured by Bio-Rad) in the usual way. After the transfer, blocking with 1% BSA-PBS was carried out at room temperature for 60 minutes. After the blocking, the monoclonal antibody was allowed to undergo overnight reaction at 4° C. After washing with PBS-Tween 20, alkaline phosphatase-labeled rabbit anti-mouse immunoglobulin was allowed to undergo 1 hour of reaction at room temperature. After the reaction, the washing was repeated and color development was effected by adding BCIP/NBT solution. The results thus obtained are shown in FIG. 1 (B). The band was found in the region of 200 kD or more.

Also, the lectin analysis was carried out by effecting blocking of the sample after its transfer on PVDF membrane in the same manner as the case of Western blotting, allowing digoxigenin-labeled lectin (manufactured by Boehringer-Mannheim) to undergo 2 hours of reaction at room temperature, carrying out washing, allowing alkaline phosphatase-labeled digoxigenin antibody (manufactured by Boehringer-Mannheim) to undergo 1 hour of reaction at room temperature, carrying out washing and then effecting color development by adding BCIP/NBT solution.

As shown in FIG. 1, it can be said that the antigen has a molecular weight of 200 kD or more based on the results of SDS-polyacrylamide gel electrophoresis and Western immunoblotting and is a glycoprotein because it is strongly stained by PAS staining.

Also, based on the lectin analysis, this is a glycoprotein which reacts strongly with MAA lectin and PNA lectin but does not react with GNA lectin, SNA lectin and DSA lectin. The results are shown in Table 1. Based on its reactivity with lectin, it seems that the sugar chain terminal structure of this antigen has NeuAc(2-3)Gal and Gal(1-3)GalNAc structures but does not have mannose, NeuAc(2-6)Gal, NeuAc(2-6)GalNAc and Gal(1-4)GlcNAc structures.

TABLE 1

Reactivity of TRD-L1 reactive antigen with lectin

| Lectin | Reactivity |
|--------|------------|
| GNA | − |
| SNA | − |
| MAA | + |
| PNA | + |
| DSA | − |

−: negative
+: positive

On the other hand, the DF-L1 reactive antigen is a glycoprotein which reacts strongly with MAA lectin, SNA lectin and DSA lectin and weakly with PNA lectin but does not react with GNA lectin, and it seems that the sugar chain terminal structure of the DF-L1 reactive antigen has NeuAc(2-3)Gal, Gal(1-3)GalNAc, NeuAc(2-6)Gal, NeuAc(2-6)GalNAc and Gal(1-4)GlcNAc structures.

Inventive Example 4

Immunohistochemical assay

Frozen blocks of lung adenocarcinoma, squamous cell carcinoma, small cell carcinoma and normal tissue were sliced to a thickness of 9 microns using a cryostat to prepare slide glass non-fixed frozen sections. Each of the frozen sections was subjected to 10 minutes of reaction with 0.5% hydrogen peroxide to effect blocking of endogenous peroxidase. This was washed with 20 mM phosphate buffer containing 0.154 M NaCl (PBS) and then subjected to 10 minutes of reaction with 10% rabbit serum in PBS. After washing again with PBS, a monoclonal antibody was added thereto to carry out 60 minutes of reaction. This was again washed with PBS and allowed to undergo reaction with peroxidase-labeled rabbit anti-mouse immunoglobulin (manufactured by Cappel) which has been diluted 200 times with PBS. After 60 minutes of the reaction and subsequent washing with PBS, a color developing kit (manufactured by Funakoshi Pharmaceutical) containing diaminobenzidine and hydrogen peroxide was added as the substrate and 15 minutes of reaction was carried out. This was washed again, subjected to nuclear staining with a hematoxylin solution, dehydrated and then embedded. In this connection, all of the above reactions were carried out at room temperature. The thus treated sections were observed under a microscope at 100× magnification, and a section in which 10% or more of cells were stained brown was judged positive. The results are shown in Table 2. As the result, the monoclonal antibody of the present invention showed highly positive reaction against lung adenocarcinoma.

TABLE 2

|  | Lung adenocarcinoma | Lung squamous cell carcinoma | Lung small cell carcinoma | Lung normal tissue |
|---|---|---|---|---|
| TRD-L1 | 5/5 | 0/5 | 0/3 | 0/2 |
| TRD-L2 | 5/5 | 0/5 | 0/3 | 0/2 |
| TRD-L3 | 5/5 | 0/5 | 0/3 | 0/2 |
| DF-L1 | 5/5 | 5/5 | 0/3 | 1/2 |

Inventive Example 5

Enzyme immunoassay

Each of normal human serum, serum of lung adenocarcinoma patient and a culture supernatant fluid of the lung adenocarcinoma established cell line Calu-3 (ATCC HTB-55) was centrifuged and the insoluble matter was removed using a 0.45 μm filter, and then the thus prepared sample was applied to an affinity chromatography column whose packing has been linked by the monoclonal antibody DF-L1, thereby effecting adsorption of the antigen, subsequently washing with 10 mM PBS (phosphate buffer, pH 7.4). After washing, the elution was effected using 3 M KSCN. After the elution, the eluate was dialyzed and concentrated to obtain DF-L1-linked antigen. The same amount of each of the thus obtained antigen (antigen containing 1 μg/ml of protein) was dispensed in 100 μl portions into wells of a 96 F aminoplate (manufactured by Sumitomo Bakelite), and their bonding was effected using glutaraldehyde in the usual way. After removing the supernatant fluid by suction, the plate was washed with PBS-Tween 20, and block (blocking) of the bound residues was carried out by adding 300 μl of 1% BSA-PBS. After removing the supernatant fluid again by suction, the plate was washed with PBS-Tween 20. A monoclonal antibody solution (1 μg/ml) was dispensed in 100 l portions into wells of the plate and allowed to undergo overnight reaction at 4° C.

After removing the supernatant fluid by suction, this was washed with PBS-Tween 20. After the washing, an anti-mouse immunoglobulin antibody-peroxidase conjugate was dispensed in 100 μl portions into the wells to carry out 2 hours of reaction at room temperature. After washing, 0.1 M citrate buffer (pH 4.2) containing O-phenylenediamine dihydrochloride and hydrogen peroxide was dispensed in 100 μl/well portions and then allowed to stand for 30 minutes at room temperature. After dispensing 2 N sulfuric acid in 50 μl/well portions, OD at 492 nm was finally measured to confirm the presence of antigen. The results are shown in Table 3. The antigen of the present invention was secreted in the serum of lung adenocarcinoma patient and the culture supernatant fluid of lung adenocarcinoma established cell line, and the monoclonal antibody of the present invention reacted with this antigen most strongly.

TABLE 3

|  | Calu-3 | Lung adenocarcinoma patient | Normal human serum |
|---|---|---|---|
|  | | Absorbance at 492 nm | |
| TRD-L1 | 0.480 | 0.478 | 0.048 |
| TRD-L2 | 0.351 | 0.422 | 0.021 |
| TRD-L3 | 1.034 | 1.271 | 0.094 |
| DF-L1 | 1.333 | 1.233 | 1.235 |

Inventive Example 6

Figure 2:
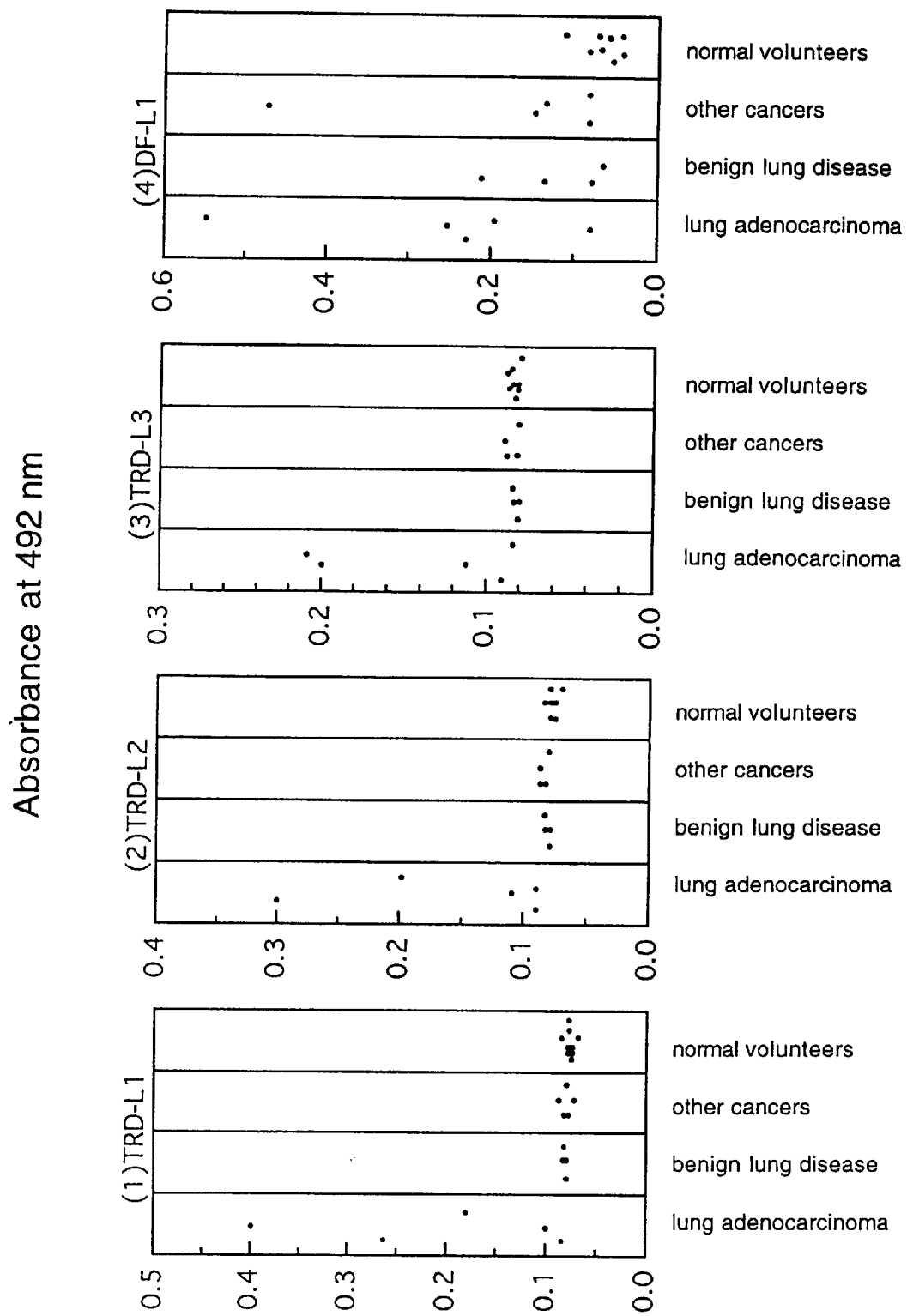
FIG. 2 shows results of the measurement of an antigen in sera of normal volunteers and patients of lung adenocarcinoma, benign lung diseases and other cancers, detected at an absorbance of 492 nm in Inventive Example 6.

Using 10 serum samples of normal volunteers, 5 serum samples of lung adenocarcinoma patients, 5 serum samples of benign lung disease patients and 5 serum samples of other cancer patients, the amount of antigen in the serum of each patient was measured by sandwich enzyme immunoassay. That is, a monoclonal antibody solution (5 μg/ml, 0.05 M carbonate buffer (pH 9.6)) was dispensed in 100 μl portions into wells of a 96 F immunoplate (manufactured by Nunc) and allowed to undergo overnight reaction at 4° C. After removing the solution by aspiration, PBS containing 1% BSA was dispensed to carry out blocking. After washing with PBS-Tween 20, each of the serum samples which has been diluted 20 times with PBS solution containing 5% BSA was dispensed in 100 μl portions into the wells to carry out 1 hour of reaction at room temperature. After washing the plate with PBS-Tween 20, peroxidase-labeled DF-L1 antibody was dispensed in 100 μl portions into the wells. After 1 hour of reaction at room temperature and subsequent washing with PBS-Tween 20, 0.1 M citrate buffer (pH 4.2) containing O-phenylenediamine dihydrochloride and hydrogen peroxide was dispensed in 100 μl/well portions and allowed to stand for 30 minutes at room temperature, and then 2 N sulfuric acid was dispensed in 50 μl/well portions. Finally measuring OD at 492 nm, the presence of antigen was confirmed. The results are shown in FIG. 2. Since the antigen of the present invention is secreted in sera of lung adenocarcinoma patients most frequently, it can be said that measurement of said antigen making use of the monoclonal antibody of the present invention is useful for the diagnosis of lung adenocarcinoma.

Inventive Example 7

Comparison of antibody characteristics

Using a DF-L1 monoclonal antibody-linked affinity chromatography, antigen was purified from a culture supernatant fluid of the lung adenocarcinoma cell line Calu-3 in the same manner as described in Inventive Example 2. Concentration of the purified antigen was measured by the method of Maimonis P. et al. (*Cancer Res.*, 51, 3838, 1991). In the same manner, antigen was purified from pooled normal human sera, and the amount of antigen in the normal human purified antigen solution was measured by the same sandwich enzyme immunoassay. After the measurement, the amount of each of these antigens was adjusted to 2.9 to 1,000 units/ml by diluting it with 10 mM PBS, and the following measurement was carried out by the method of Maimons P. et al. in which DF-L1 antibody was used and the method of Inventive Example 6 in which TRD-L1 antibody was used.

Figure 3:
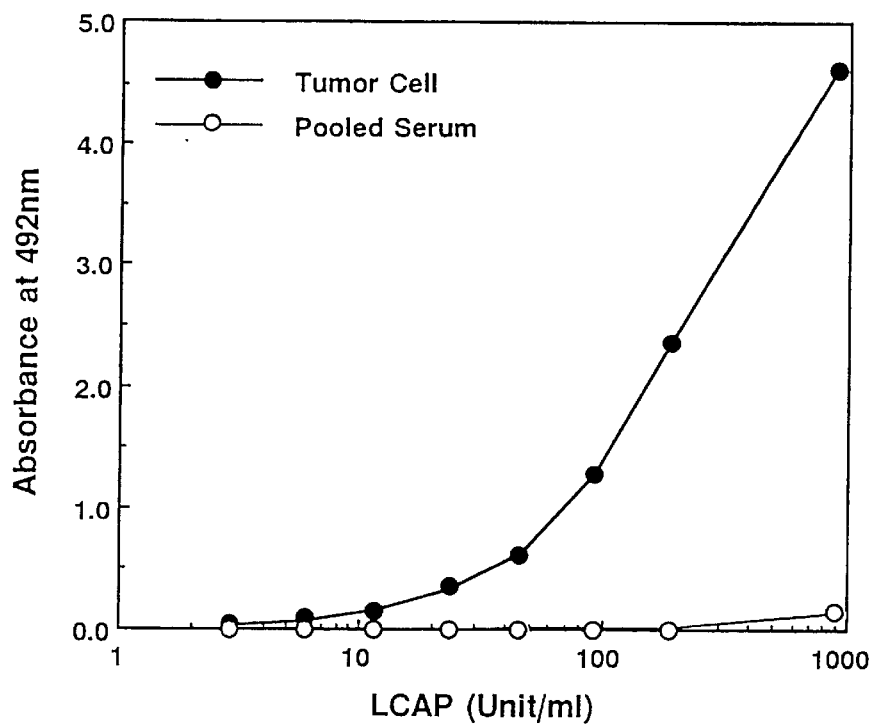
FIGS. 3 (A) and (B) shows results of the absorbance measurement in which antigens recognizable by DF-L1 or TDR-L1 and prepared from cancer cells and normal volunteer sera are measured, wherein FIG. 3 (A) is a case of the use of TDR-L1 and FIG. 3 (B) is a case of the use of DF-L1.
Figure 3:
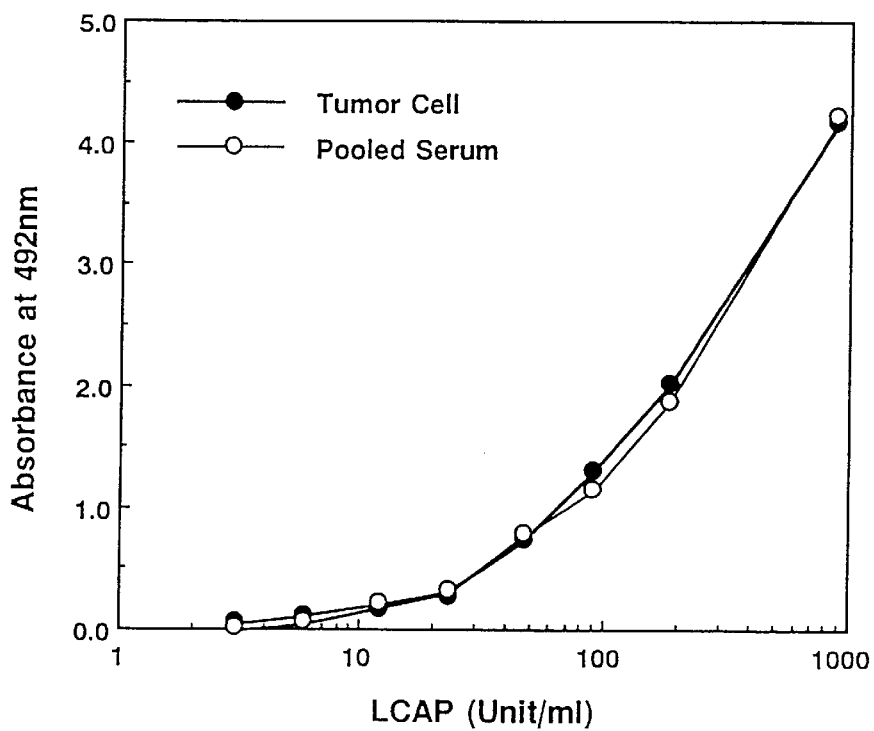

That is, each of the antibody solutions (5 μg/ml, 0.5 M carbonate buffer (pH 9.6)) of DF-L1 antibody and TRD-L1 antibody was dispensed in 100 μl portions into wells of two 96 F immunoplates (manufactured by Nunc) and allowed to undergo overnight reaction at 4° C. After removing the solution by suction, PBS containing 1% BSA was dispensed to carry out blocking. After washing with PBS-Tween 20 solution, each of the diluted cell-derived and normal human-derived antigen solutions was dispensed to carry out 1 hour of reaction at room temperature. After washing with PBS-Tween 20 solution, peroxidase-labeled DF-L1 antibody was dispensed in 100 μl portions into the wells. After 1 hour of reaction at room temperature and subsequent washing with PBS-Tween 20 solution, 0.1 M citrate buffer (pH 4.2) containing O-phenylenediamine dihydrochloride and hydrogen peroxide was dispensed in 100 μl/well portions and allowed to stand for 30 minutes at room temperature, and then 2 N sulfuric acid was dispensed in 50 μl/well portions. Finally measuring OD at 492 nm, the presence of antigen was confirmed. The amount of antigen in serum sample is shown in FIG. 3 as the strength of color development, namely as the absorbance at a wave length of 492 nm. In this case, the amount of antigen shown in the drawing was measured by the method reported by Maimonis et al.

Results

In FIG. 3, the reactivity of cell-derived and normal human-derived antigen solutions obtained in Inventive Example 7 by respective assay methods was shown as the strength of color development. That is, in comparison with the assay method in which DF-L1 antibody is solely used, the assay method of the present invention in which TRD-L1 antibody is used recognizes the antigen specific to lung adenocarcinoma cells, so that measurement of said antigen making use of this antibody is useful for the diagnosis of lung adenocarcinoma, and this information can be used broadly in the diagnosis of cancers including metastatic cancers.

Inventive Example 8

Detailed evaluation by samples from patients

In order to confirm clinical usefulness of the TRD-L1-aided assay method, the amount of antigen in serum of each patient was measured by the same method of Inventive Example 6, using 46 serum samples of normal volunteers (Normal), 425 serum samples of lung adenocarcinoma patients (Lung Cancer), 240 serum samples of benign lung disease patients (Benign), 27 lung adenocarcinoma serum samples (Adeno), 9 squamous cell carcinoma serum samples (Sque), 5 small cell carcinoma serum samples (Small), 2 large cell carcinoma serum samples (Large), 45 serum samples of stomach cancer patients (Stomach), 44 serum samples of breast cancer patients (Breast), 21 serum samples of colon cancer patients (Colon) and 5 serum samples of other cancer patients (Misc). The amount of antigen was calculated by deciding previously measured samples of patients as optional values and using the values as standards.

That is, a TRD-L1 monoclonal antibody solution (5 μg/ml, 0.5 M carbonate buffer (pH9.6)) was dispensed in 100 μl portions into wells of a 96 F immunoplate (manufactured by Nunc), subsequently carrying out blocking. After washing with PBS-Tween 20 solution, each of the serum samples which has been diluted 6 times with PBS solution containing 5% BSA and four standard solutions having known concentrations (0, 20, 100, 200 units/ml) was dispensed in 120 μl portions into the wells to carry out 1 hour of reaction at room temperature. After washing with PBS-Tween 20 solution, peroxidase-labeled DF-L1 antibody was dispensed in 100 μl portions into the wells. After 1 hour of reaction at room temperature and subsequent washing with PBS-Tween 20 solution, 0.1 M citrate buffer (pH 4.2) containing O-phenylenediamine dihydrochloride and hydrogen peroxide was dispensed in 100 μl/well portions and allowed to stand for 30 minutes at room temperature, and then 2 N sulfuric acid was dispensed in 50 μl/well portions. The amount of antigen in serum samples of patients was determined by measuring the strength of color development, namely absorbance at a wave length of 492 nm, and comparing the value with a calibration curve prepared from the concentration of standards and the absorbance.

When the serum concentration exceeded 200 units/ml, the measurement was carried out after further dilution.

Results

Figure 4:
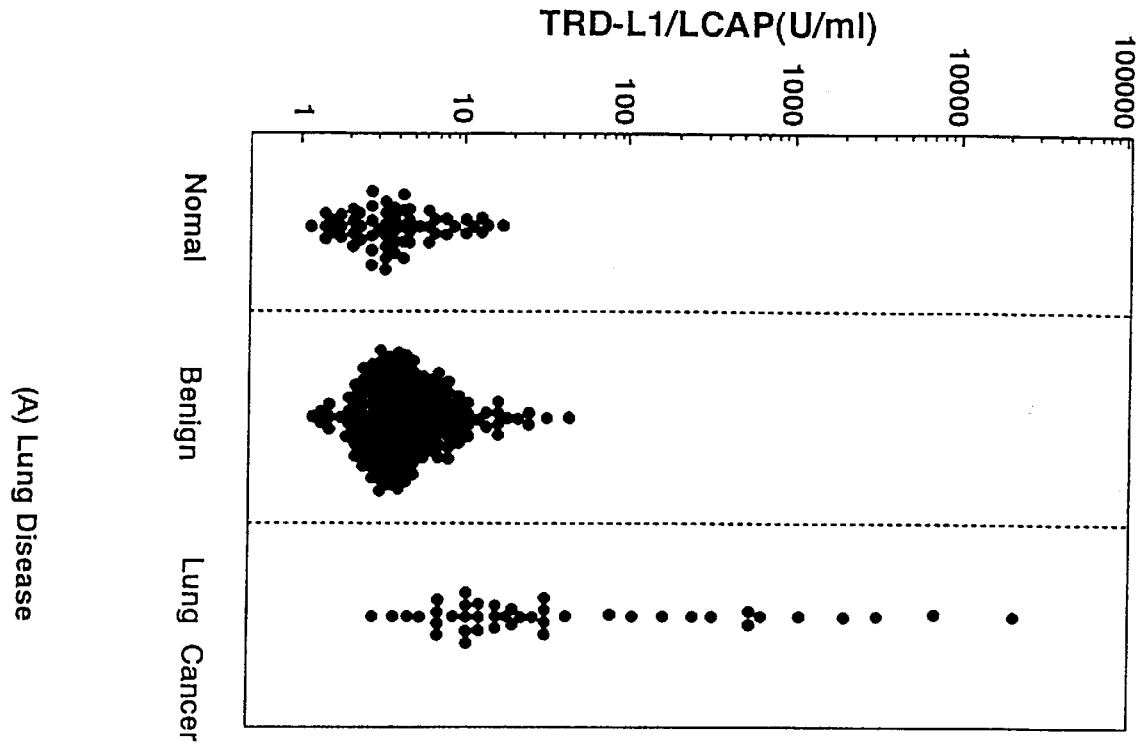
FIG. 4 (A) and FIGS. 4 (B) (C) shows specificity of measuring systems in which the TRD-L1 antibody is used, wherein FIG. 4 (A) shows specificity in lung diseases, and FIG. 4 (B) in lung cancers and FIG. 4 (C) in other cancers.
Figure 4:
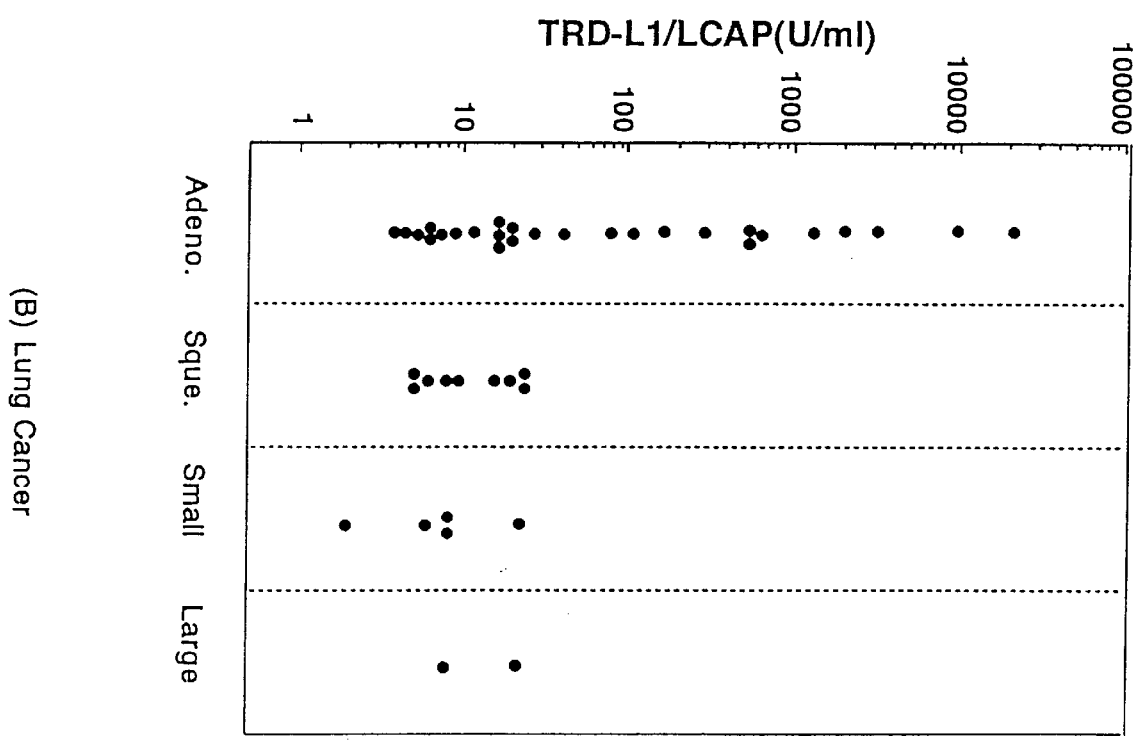
Figure 4:
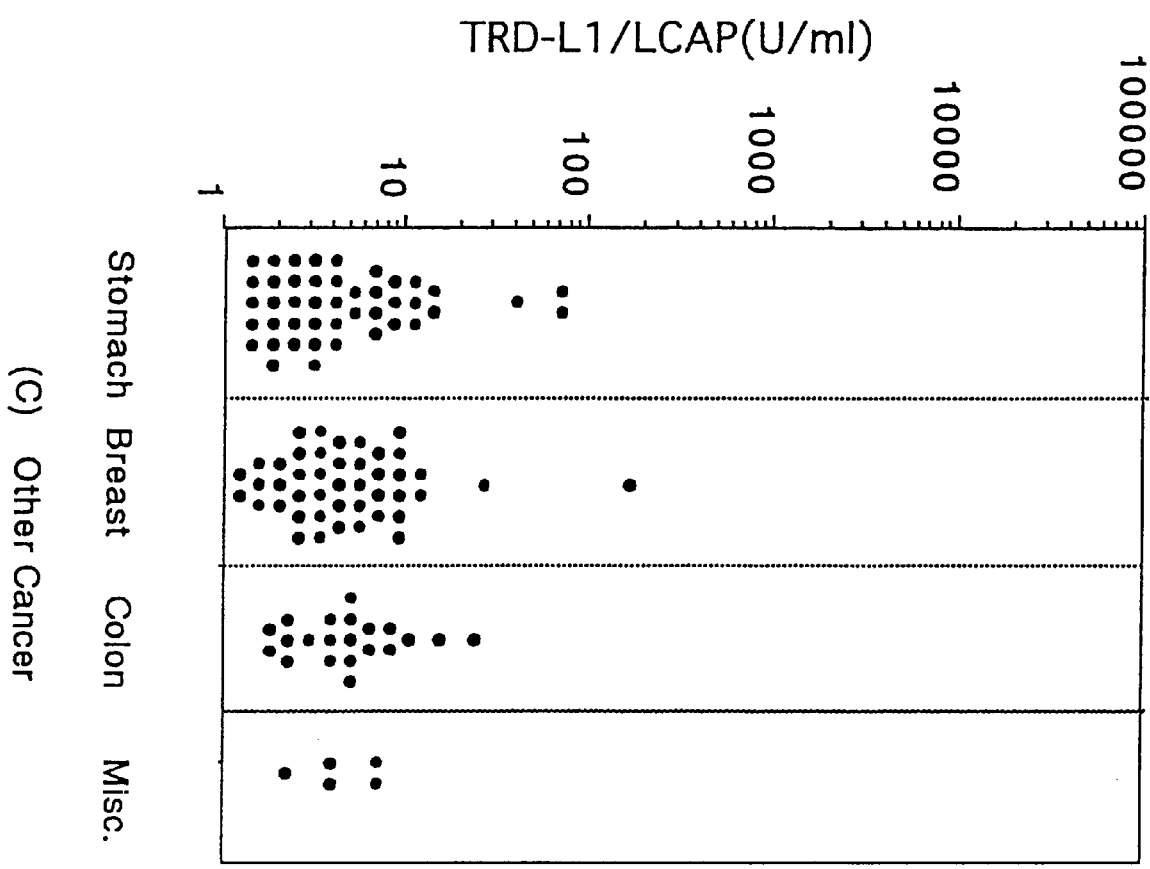
Figure 5:
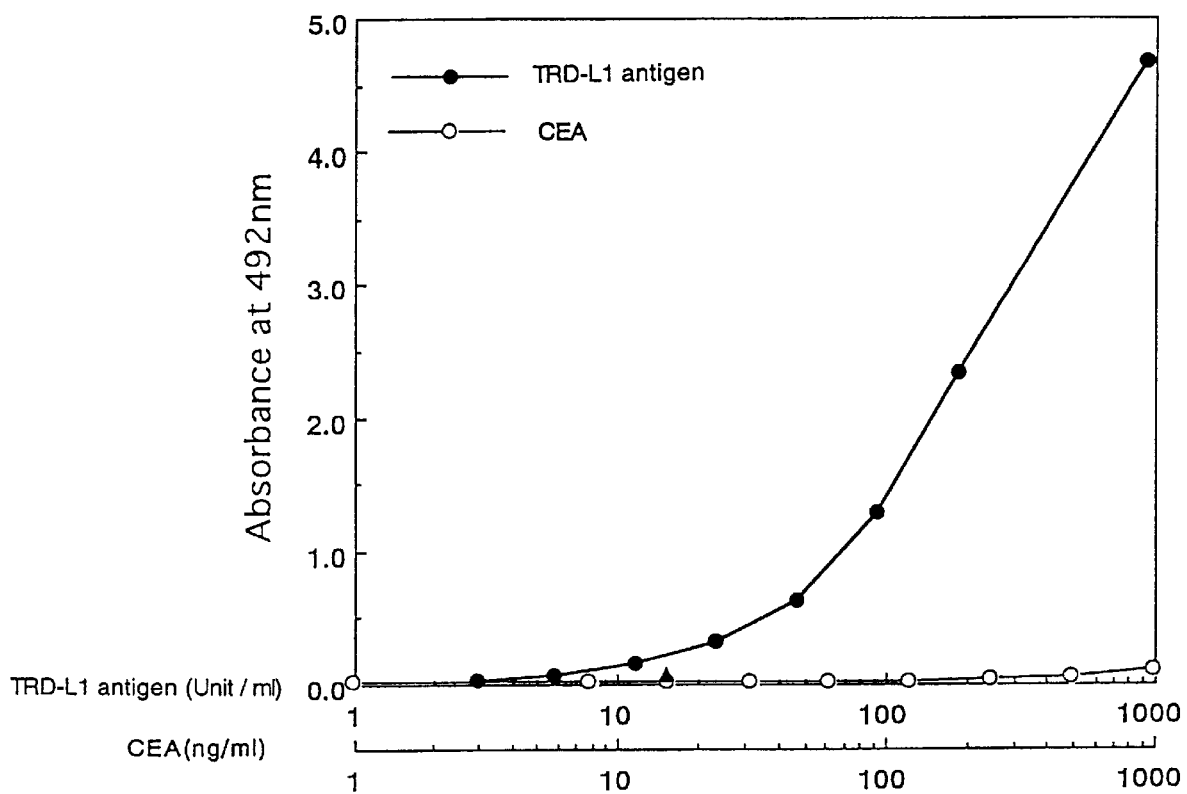
FIG. 5, FIG. 6, FIG. 7, FIG. 8 and FIG. 9 respectively show results of the measurement of CEA, CA 19-9, CA 125, CA 50 and CA 15-3, obtained in Inventive Example 8.
Figure 6:
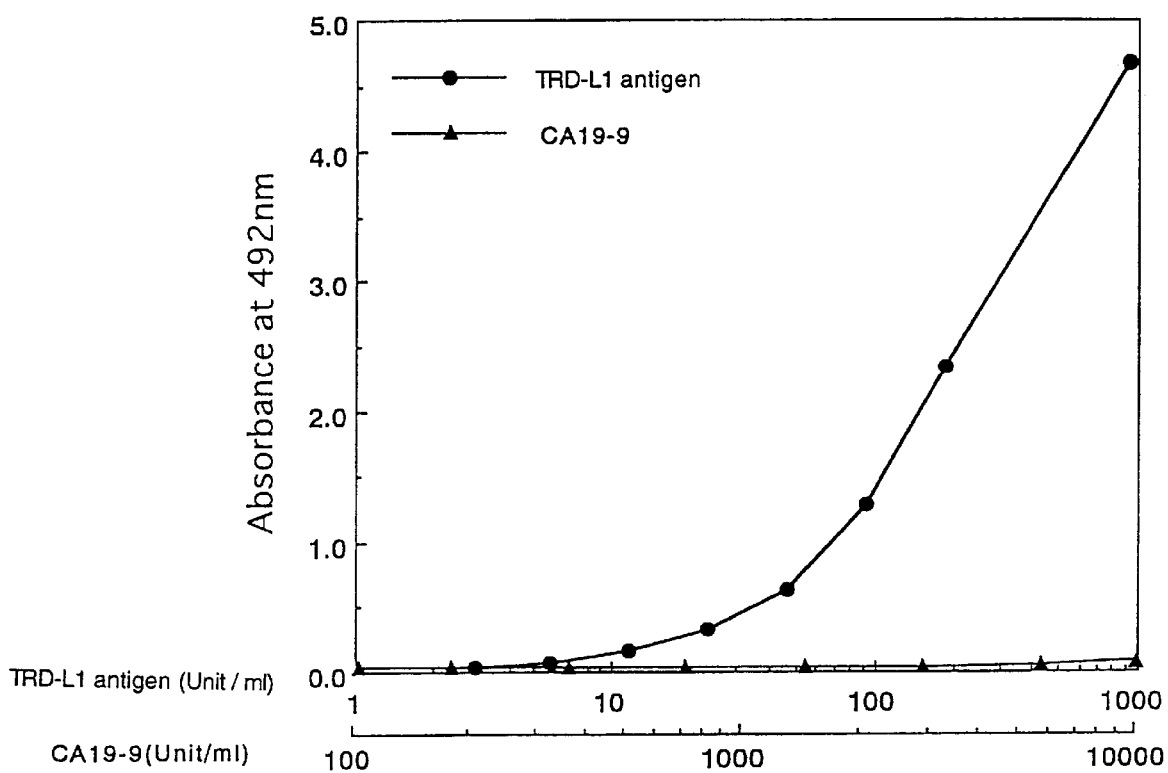
Figure 7:
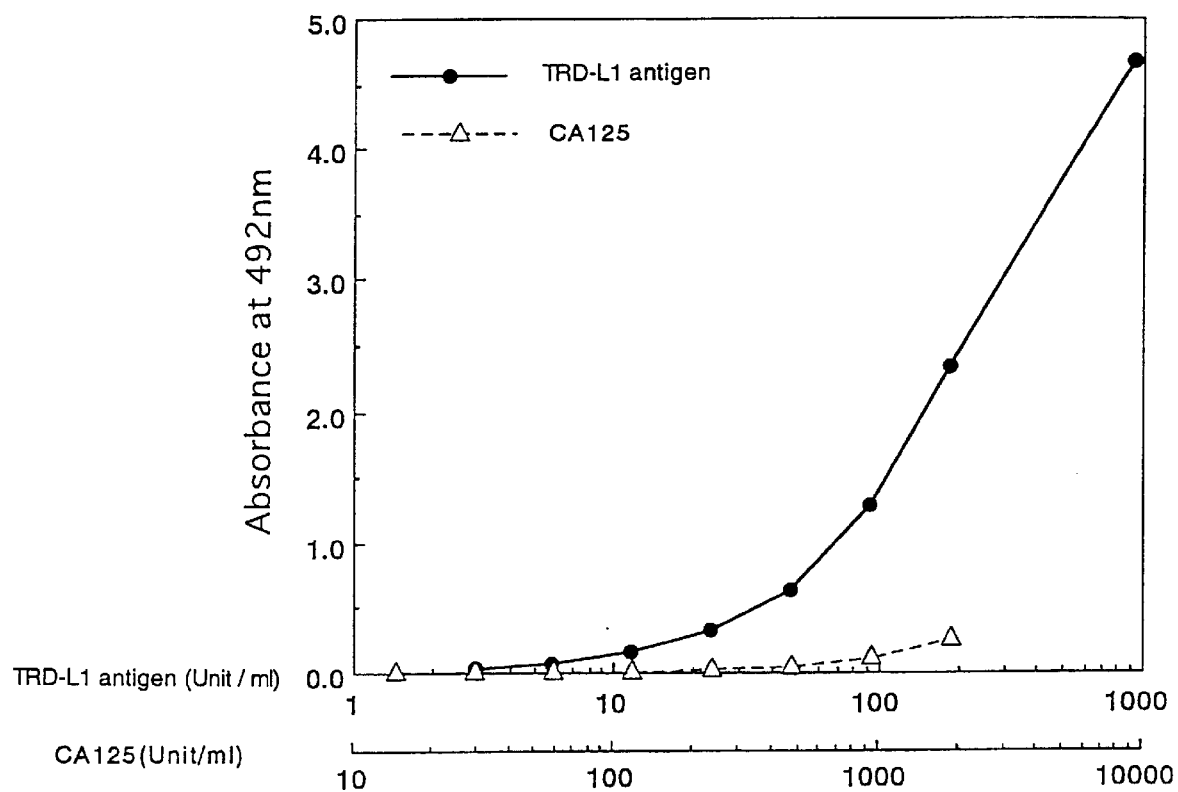
Figure 8:
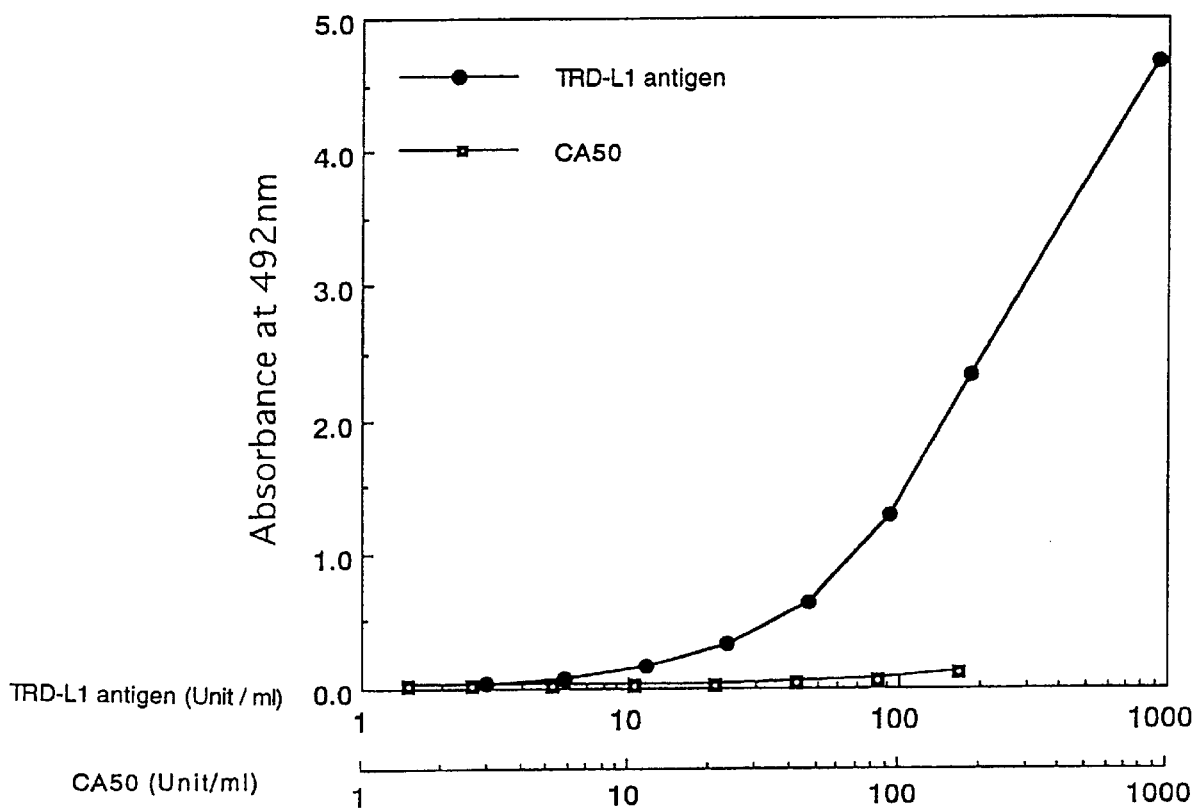
Figure 9:
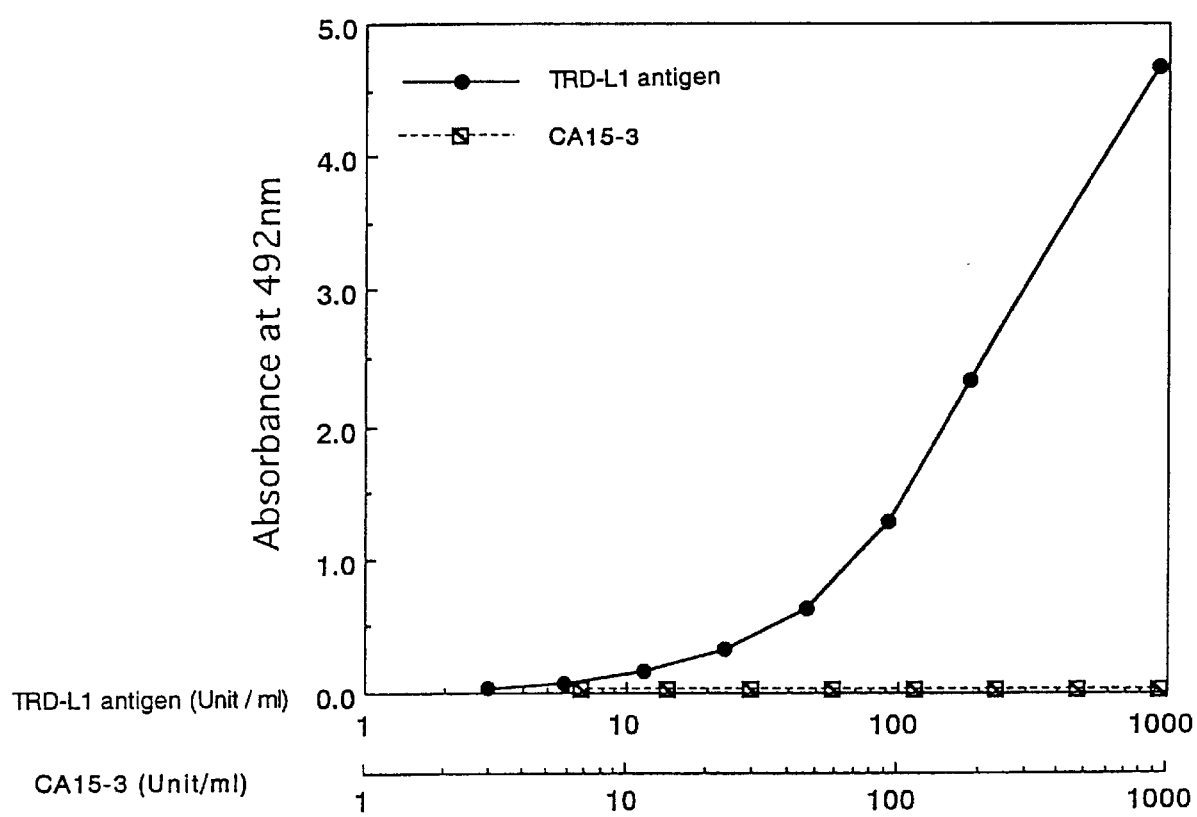

FIG. 4 shows the amount of antigen in sera of normal volunteers and patients of lung adenocarcinoma, benign lung diseases and other cancers, obtained in Inventive Example 8. Since said antigen of the present invention is secreted in sera of lung adenocarcinoma patients most frequently, measurement of said antigen making use of said monoclonal antibody is useful for the diagnosis of lung adenocarcinoma.

Inventive Example 9

Reactivity with other tumor antigens

Reactivity of the antibody and assay method of the present invention with known tumor antigens CEA, CA19-

9, CA125, CA50 and CA15-3, glycoprotein antigens similar to the inventive antigen, was measured by the same method of Inventive Example 6. Each antigen was diluted with 10 mM PBS, and the amount of antigen was measured as the absorbance at a wave length of 492 nm.

That is, a TRD-L1 monoclonal antibody solution (5 μg/ml, 0.5 M carbonate buffer (pH 9.6)) was dispensed in 100 μl portions into wells of a 96 F immunoplate (manufactured by Nunc) and allowed to undergo overnight reaction at 4° C. After removing the solution by suction, PBS containing 1% BSA was dispensed to carry out blocking. After washing with PBS-Tween 20 solution, each of the antigen solutions was dispensed in 100 μl portions into the wells to carry out 1 hour of reaction at room temperature. After washing with PBS-Tween 20 solution, peroxidase-labeled DF-L1 antibody was dispensed in 100 μl portions into the wells. After 1 hour of reaction at room temperature and subsequent washing with PBS-Tween 20 solution, 0.1 M citrate buffer (pH 4.2) containing O-phenylenediamine dihydrochloride and hydrogen peroxide was dispensed in 100 μl/well portions and allowed to stand for 30 minutes at room temperature, and then 2 N sulfuric acid was dispensed in 50 μl/well portions. Finally measuring OD at 492 nm, the presence of antigen was confirmed.

Results

FIG. 5 to FIG. 9 are graphs showing results of the measurement of TRD-L1 antibody linked to CEA, CA19-9, CA125, CA50 or CA15-3, obtained in Inventive Example 9, which are compared with the results of TRD-L1 antigen. That is, said antigen and antibody of the present invention are different from other glycoprotein tumor antigens.

INDUSTRIAL APPLICABILITY

Novel monoclonal antibody and antigen can be obtained by the present invention, and an immunoassay method which uses said monoclonal antibody and antigen renders possible definite diagnosis and prognostic judgment of lung adenocarcinoma by detecting lung adenocarcinoma cells in tissues and measuring the amount of antigen in human body fluids such as blood.

We claim:

1. A monoclonal antibody or antigen binding fragment thereof, which antibody specifically binds to a human pulmonary adenocarcinoma cell antigen wherein said monoclonal antibody is produced by a hybridoma selected from the group consisting of FERM BP-5383, FERM P-14879 and FERM P-14880.

2. The monoclonal antibody of claim 1, wherein said antibody is of the IgM isotype.

3. The monoclonal antibody or fragment of claim 1, wherein said fragment is selected from the group consisting of a Fab, F(ab)$_2$, and a Fv fragment.

4. An immunoassay method for diagnosis of human pulmonary adenocarcinoma which comprises contacting a sample of a subject suspected of having human pulmonary adenocarcinoma with a monoclonal antibody or fragment according to claim 1 and correlating whether the subject has pulmonary adenocarcinoma based on the binding or absence of binding of said antibody to any human pulmonary adenocarcinoma antigen contained in said sample, wherein said human pulmonary adenocarcinoma antigen is the antigen specifically bound by said monoclonal antibody or fragment thereof.

5. The method of claim 4, wherein said antibody or fragment is directly or indirectly attached to a detectable label.

6. The method of claim 4, wherein said immunoassay method is a sandwich enzyme assay method.

7. The method of claim 5, wherein said label is an enzyme.

8. The method of claim 4, wherein said sample is a human sera sample.

9. The monoclonal antibody or fragment of claim 1, which further comprises a detectable label.

* * * * *

UNITED STATES PATENT AND TRADEMARK OFFICE
CERTIFICATE OF CORRECTION

PATENT NO. : 6,015,680
DATED : January 18, 2000
INVENTOR(S) : Kouichi TSUJI et al It is certified that error appears in the above-identified patent and that said Letters Patent is hereby corrected as shown below:

In Column 12, line 21, delete "100 1" and insert -- 100 µl --.

Signed and Sealed this

Tenth Day of October, 2000

Attest:

Q. TODD DICKINSON

*Attesting Officer*          *Director of Patents and Trademarks*